(12) United States Patent
Havla et al.

(10) Patent No.: US 11,557,452 B2
(45) Date of Patent: Jan. 17, 2023

(54) X-RAY EMITTER

(71) Applicant: Siemens Healthcare GmbH, Erlangen (DE)

(72) Inventors: Lukas Havla, Forchheim (DE); Anja Fritzler, Erlangen (DE); Peter Roehrer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 136 days.

(21) Appl. No.: 17/013,990

(22) Filed: Sep. 8, 2020

(65) Prior Publication Data

US 2021/0082655 A1 Mar. 18, 2021

(30) Foreign Application Priority Data

Sep. 12, 2019 (EP) ...................... 19196954

(51) Int. Cl.
*H01J 35/10* (2006.01)
*H01J 35/18* (2006.01)
(Continued)

(52) U.S. Cl.
CPC .......... *H01J 35/106* (2013.01); *A61B 6/4488* (2013.01); *H01J 35/18* (2013.01);
(Continued)

(58) Field of Classification Search
CPC ............. H01J 35/106; H01J 2235/1216; H01J 2235/127; A61B 6/4488; H05G 1/025
See application file for complete search history.

(56) References Cited

U.S. PATENT DOCUMENTS 2,900,543 A * 8/1959 Heuse ..................... H01J 35/10
378/143
4,355,410 A 10/1982 Sullins
(Continued)

FOREIGN PATENT DOCUMENTS

DE 3587087 T2 9/1993
DE 29823735 U1 11/1999
(Continued)

OTHER PUBLICATIONS

Anonymously Disclosed "An X Ray Tube with rotating vacuum insert and stationary conventional cathod" ip.com Journal, ip.com Inc.; West Henrietta, NY, US; Apr. 24, 2007 // ISSN:1533-0001.
(Continued)

*Primary Examiner* — Chih-Cheng Kao
(74) *Attorney, Agent, or Firm* — Harness, Dickey & Pierce, P.L.C.

(57) ABSTRACT

An x-ray emitter includes an x-ray tube and an x-ray emitter housing. In an embodiment, the x-ray tube includes an evacuated x-ray tube housing, a cathode for emitting electrons and an anode for generating x-rays as a function of the electrons. Further, in an embodiment, the x-ray emitter housing includes the x-ray tube and outside of the x-ray tube, a gaseous cooling medium. In an embodiment, the x-ray emitter further includes a compressor for a forced convection of the gaseous cooling medium for cooling the x-ray tube, a pressure ratio between the intake side and pressure side of the compressor being greater than 1.3.

18 Claims, 3 Drawing Sheets

(51) Int. Cl.
*H05G 1/02* (2006.01)
*A61B 6/00* (2006.01)
*A61B 6/03* (2006.01)

(52) U.S. Cl.
CPC .............. *H05G 1/025* (2013.01); *A61B 6/035* (2013.01); *H01J 2235/127* (2013.01); *H01J 2235/1216* (2013.01); *H01J 2235/1283* (2013.01)

(56) References Cited

U.S. PATENT DOCUMENTS

| | | |
|---|---|---|
| 4,788,705 A | 11/1988 | Anderson |
| 4,821,305 A | 4/1989 | Anderson |
| 4,884,292 A | 11/1989 | Klostermann |
| 5,802,140 A | 9/1998 | Virshup et al. |
| 6,134,299 A | 10/2000 | Artig |
| 6,445,769 B1 | 9/2002 | Panasik et al. |
| 2004/0264645 A1* | 12/2004 | Freudenberger .... H01J 35/1024 378/130 |
| 2007/0140420 A1* | 6/2007 | Radley .................... H01J 35/12 378/45 |
| 2009/0225951 A1* | 9/2009 | Wandke ................. H01J 35/16 378/141 |
| 2010/0260323 A1 | 10/2010 | Legall et al. |
| 2011/0158382 A1* | 6/2011 | Sahin Nomaler .... A61B 6/4435 378/21 |
| 2013/0034207 A1* | 2/2013 | Aoki ...................... H01J 35/18 378/140 |
| 2015/0124936 A1 | 5/2015 | Anno et al. |
| 2015/0272525 A1* | 10/2015 | Kühn ..................... H05G 1/025 378/199 |

FOREIGN PATENT DOCUMENTS

| | | |
|---|---|---|
| DE | 69825248 T2 | 12/2004 |
| EP | 2869672 A1 | 5/2015 |
| GB | 1228446 A | 4/1971 |
| JP | 05-000136 A * | 1/1993 |
| JP | H05136 A | 1/1993 |
| JP | 2015032512 A | 2/2015 |
| WO | WO 02059932 A2 | 8/2002 |

OTHER PUBLICATIONS

European Search Report for European Patent Application No. 19196954 dated Mar. 13, 2020.

* cited by examiner

X-RAY EMITTER

PRIORITY STATEMENT

The present application hereby claims priority under 35 U.S.C. § 119 to European patent application number EP 19196954.2 filed Sep. 12, 2019, the entire contents of which are hereby incorporated herein by reference.

FIELD

Various example embodiments of the invention generally relate to an x-ray emitter and a computed tomography device.

BACKGROUND

An x-ray emitter usually has an x-ray tube for generating x-rays, wherefore in particular the x-ray tube is cooled. A liquid cooling medium, in particular oil, is typically used for cooling the x-ray tube. The x-ray tube can be actively or passively cooled with the liquid cooling medium. With the passive cooling with the liquid cooling medium, the x-ray tube is cooled in particular via convection. With the active cooling with the liquid cooling medium, a cooled liquid cooling medium is typically fed to the x-ray tube and a heated liquid cooling medium is removed.

The x-ray emitter typically requires a heat exchanger for transferring thermal energy for the active cooling with the liquid cooling medium. In addition to the heat exchanger, an x-ray emitter of this type typically has pipes and corresponding couplings, as a result of which a complexity and/or a weight of the x-ray emitter is usually significantly increased.

DE 35 87 087 T2 discloses an x-ray emitter, in which on a front face the evacuated x-ray tube housing has a structure which forms channels for a liquid or a gaseous cooling medium. An anode is arranged on the inner surface of this structure so that the rear side of the anode is cooled by the flowing cooling medium.

U.S. Pat. Nos. 4,355,410, 4,884,292 and DE 698 25 248 T2 describe in each case an x-ray emitter housing, in which an x-ray tube and a ventilator are arranged. The ventilator generates an air flow, as a result of which the x-ray tube is cooled during operation. According to DE 698 25 248 T2, the evacuated x-ray tube housing of the x-ray tube has cooling fins for improving the air cooling on its outer periphery.

U.S. Pat. No. 6,134,299 discloses a device for generating x-ray radiation, in which an air flow is guided around or in an x-ray tube housing via cooling fins.

WO 02/059932 A2 and JP 2015032512 A disclose in each case an x-ray emitter which comprises an x-ray emitter housing in which an x-ray tube and a ventilator are arranged. During operation, a ventilator generates an air flow in the x-ray emitter housing, as a result of which the x-ray tube is cooled from the outside.

With the afore-described x-ray emitters with a gaseous cooling medium (e.g. air), the circulation of the gaseous cooling medium typically takes place via a ventilator which is arranged outside of the evacuated x-ray tube housing in the x-ray emitter housing. With a ventilator of this type, only minimal heat dissipation, in particular cooling, can be realized so that despite the complicated design solution, the oil cooling described continues to be used regularly for x-ray emitters.

DE 298 23 735 U1 describes a rotary piston x-ray emitter with a primary coolant circuit which comprises an external heat exchanger. A gaseous coolant, which at the same time takes over the high-voltage isolation of a rotating rotary piston x-ray tube in the x-ray emitter housing, circulates in the coolant circuit. The coolant is supplied near the axis and is drawn from the x-ray emitter housing in the anode-side region. The anode forming the base of the rotating rotary piston is preferably provided with a profiling which enlarges the cooling surface. This profiling generates a convection of the gaseous coolant. This convection is at best comparable with a convection which can be achieved via a ventilator. A preferred coolant is sulfur hexafluoride.

SUMMARY

Embodiments of the invention specify an x-ray emitter and a computed tomography device in which the cooling is improved.

At least one embodiment of the inventive x-ray emitter comprises:

an x-ray tube;
an x-ray emitter housing,
wherein the x-ray tube has an evacuated x-ray tube housing, a cathode for emitting electrons and an anode for generating x-rays as a function of the electrons,
wherein the x-ray emitter housing has the x-ray tube and outside of the x-ray tube a gaseous cooling medium; and
a compressor for a forced convection of the gaseous cooling medium for cooling the x-ray tube, wherein a pressure ratio between the intake side and pressure side of the compressor is greater than 1.3.

At least one embodiment is directed to a computed tomography device, comprising:

a stationary carrier ring and a rotating carrier ring, wherein the rotating carrier ring includes an x-ray emitter of an embodiment and an x-ray detector.

At least one embodiment is directed to a n x-ray emitter, comprising:

an x-ray tube, the x-ray tube including an evacuated x-ray tube housing, a cathode for emitting electrons and an anode for generating x-rays as a function of the electrons;
an x-ray emitter housing, housing the x-ray tube and external to the x-ray tube, including a gaseous cooling medium; and
a compressor for a forced convection of the gaseous cooling medium for cooling the x-ray tube, a pressure ratio between an intake side and a pressure side of the compressor being greater than 1.3.

BRIEF DESCRIPTION OF THE DRAWINGS

The invention is described and explained in more detail on the basis of the example embodiments shown in the figures. In principle, structures and units which essentially remain the same are identified in the following description of the figures with the same reference characters as in the first occurrence of the relevant structure or unit.

In the drawings.

DETAILED DESCRIPTION OF THE EXAMPLE EMBODIMENTS

Figure 1:
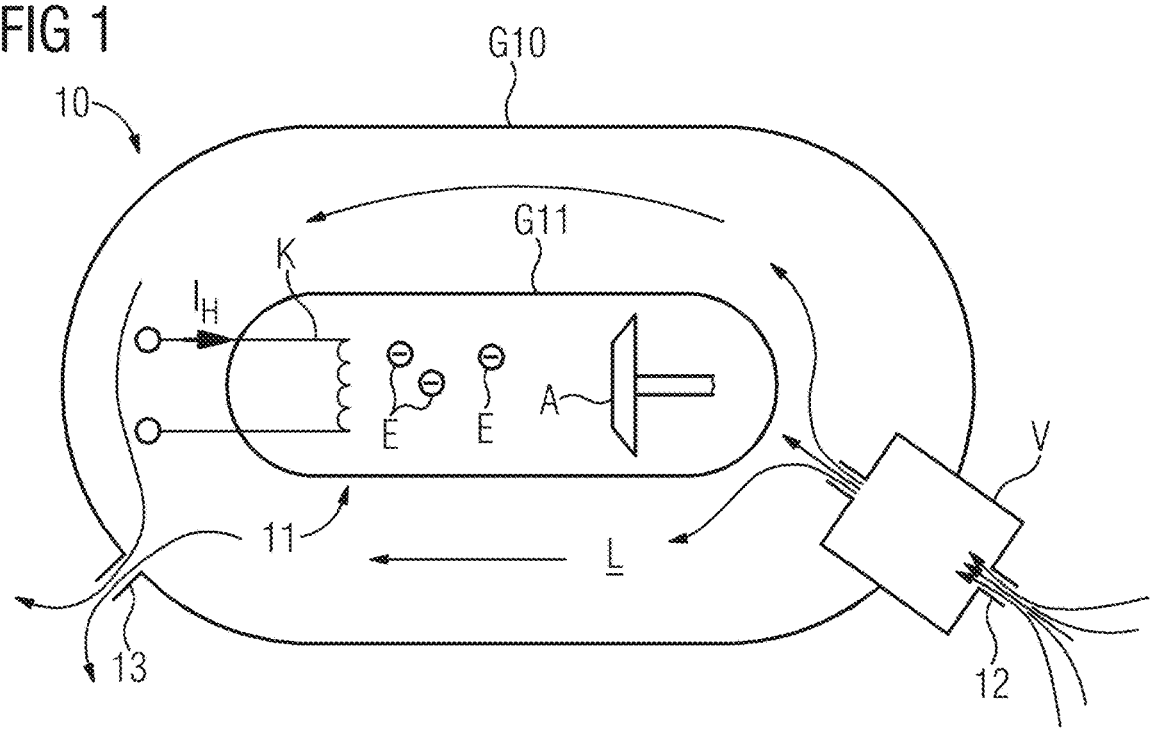
FIG. 1 shows an x-ray emitter 10 in a first example embodiment.

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, or other electrical devices, or the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling. A communication between devices may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv)

source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive x-ray emitter comprises:

an x-ray tube;
an x-ray emitter housing,
wherein the x-ray tube has an evacuated x-ray tube housing, a cathode for emitting electrons and an anode for generating x-rays as a function of the electrons,
wherein the x-ray emitter housing has the x-ray tube and outside of the x-ray tube a gaseous cooling medium; and
a compressor for a forced convection of the gaseous cooling medium for cooling the x-ray tube, wherein a pressure ratio between the intake side and pressure side of the compressor is greater than 1.3.

One advantage of the x-ray emitter is that the cooling of the x-ray emitter, in particular of the x-ray tube, with the gaseous cooling medium enables a weight saving of more than 10%, preferably more than 30%, compared with an x-ray emitter cooled with a liquid cooling medium. The x-ray emitter with the compressor is typically lighter than a conventional x-ray emitter. A further advantage is that a scattering of the x-rays by the gaseous cooling medium is significantly less than a scattering of the x-rays by the liquid cooling medium, as a result of which an image quality of an image acquired via the x-rays is preferably increased. This advantageously dispenses with a disposal problem of the liquid cooling medium, in that the compressor provides the gaseous cooling medium for cooling purposes.

The x-ray emitter can be used in a clinical and/or medical environment. It is essentially conceivable for the x-ray emitter to be used for a material testing and/or for a non-medical fluoroscopy of objects outside of the clinical and/or medical environment, in particular in a security environment.

The x-ray emitter housing usually has metal and/or glass and/or is essentially cylindrical and/or funnel-shaped. The x-ray tube, in particular the evacuated x-ray tube housing, is typically arranged within the x-ray emitter housing. The x-ray tube is typically not embodied as a stationary anode x-ray tube. At least the anode therefore usually rotates relative to the x-ray emitter housing.

The cathode can have an emitter for emitting the electrons and/or a focusing head. The emitter can be a helical emitter, a flat emitter, a field effect emitter, an emitter which can be heated directly or indirectly or a combination of the same.

The cathode and/or the anode are typically arranged within the evacuated x-ray tube housing of the x-ray tube and/or are aligned with one another. The electrons are usually accelerated from the cathode to the anode with an acceleration voltage. The acceleration voltage is typically greater than 10 kV and less than 200 kV, in particular between 60 kV and 150 kV. The x-rays are usually generated when the accelerated electrons interact with the anode. The anode typically has tungsten, gold, rhenium, rhodium, molybdenum and/or an alloy of the previous elements. It is basically conceivable for the x-ray tube to have the focusing head and/or an electromagnetic deflection unit for deflecting, in particular for focusing, the emitted electrons. Less than 5% of kinetic energy of the accelerated electrons is usually converted into x-rays, wherein the remaining energy is produced in the form of heat in particular on the anode. The anode must typically be cooled the most.

The x-ray tube housing is typically sealed in an air-tight manner. While the cathode and the anode are arranged in the evacuated x-ray tube housing, the gaseous cooling medium is typically outside of the x-ray tube and inside of the x-ray emitter housing. The gaseous cooling medium usually has air, in particular dried air, nitrogen, oxygen, neon, carbon dioxide, sulfur hexafluoride and/or a mixture of the previous elements. It is in principle conceivable for the gaseous cooling medium to consist exclusively of air. The x-ray tube, in particular the x-ray tube housing and/or the anode and/or the cathode, are preferably cooled via the gaseous cooling medium. The cooling is carried out in particular without a liquid cooling medium. The x-ray tube can preferably be cooled via the compressor so that continuous operation of the x-ray emitter, in the medical field for instance, is enabled. The continuous operation of the x-ray emitter comprises for instance a number of consecutive imaging examinations with x-rays of a patient without a cooling pause and/or consecutive imaging examinations with x-rays of a number of patients without a cooling pause. A thermal transition coefficient effected by the compressor within the x-ray emitter amounts in particular to at least 300 $W/(K^*m^2)$, preferably at least 1000 $W/(K^*m^2)$, particularly advantageously at least 1500 $W/(K^*m^2)$.

It is conceivable that the x-ray emitter housing has in particular a supply air opening and an air discharge opening. The supply air opening can in particular be on the intake side of the compressor. The air discharge opening can in particular be on the pressure side of the compressor. The cooling is carried out in particular by the forced convection, wherein heat is transmitted away from the x-ray tube via the gaseous cooling medium. The gaseous cooling medium is in particular warmer at the air discharge opening than at the supply air opening. The gaseous cooling medium flows in particular from the supply air opening to the air discharge opening.

The thermal transition coefficient typically correlates with a pressure ratio of the compressor. On the pressure side of the compressor the pressure is preferably higher than the pressure on the intake side by at least 0.5 bar, preferably by 1 bar, particularly advantageously by 2 bar or 4 bar. If there is an atmospheric pressure of approx. 1 bar on the intake side of the compressor and the pressure is approx. 1.5 bar on the pressure side, then the pressure ratio amounts to 1.5. In this case the pressure ratio of the compressor is therefore greater than 1.3. In a further example embodiment, the pressure ratio is greater than 2, preferably greater than 4, particularly advantageously greater than 8. The pressure ratio can in particular be at its greatest at the level of the anode on the exterior of the x-ray tube housing.

The compressor can be active or passive. The passive compressor has for instance a passive device which forces the convection in particular on account of the external condition and/or shape. The active compressor has for instance an active device with compressor elements, which compressor elements force the convection in particular via a direct or indirect supply of electrical or mechanical power. The active compressor can have for instance in addition the passive device of the passive compressor.

One embodiment provides that the x-ray emitter housing and the x-ray tube housing are embodied as turbine-shaped compressors for forcing the convection. This embodiment may in particular be advantageous since the convection can preferably be forced passively. In this embodiment the turbine-shaped compressor is a passive compressor. In order to force the convection, the turbine-shaped compressor can in particular have a tapering cross-section and/or be funnel-shaped. An interior of the x-ray emitter housing and/or an exterior of the x-ray tube housing can have a profiling for forcing the convection. In particular for an x-ray emitter with a comparatively low power and corresponding thermal development, passively forced convection may be sufficient. A further advantage of this embodiment may be that wear of the x-ray emitter is reduced compared with a conventional x-ray emitter with a ventilator. A thermal transition coefficient of this embodiment is in particular greater than 300 $W/(K^*m^2)$, preferably greater than 1500 $W/(K^*m^2)$.

One embodiment provides that the anode rotates with a shaft which rotates relative to the x-ray emitter housing, wherein the compressor has a number of turbine blades for forcing the convection and wherein the number of turbine blades are mounted on the rotating shaft so that a rotational speed of the anode and a rotational speed of the number of turbine blades depend on one another. The rotational speed of the anode correlates in particular with the rotational speed of the number of turbine blades. The compressor with the number of rotating turbine blades is in particular an active compressor. This embodiment is in particular advantageous if the number of turbine blades and the anode are preferably fixedly connected, in particular mechanically coupled, via the rotating shaft. The number of turbine blades rotate in particular with the anode and/or with the rotating shaft, typically with a correlated or with the same rotational speed. It is in principle conceivable for the number of turbine blades and the anode to be coupled by way of a transmission with a gear transmission ratio in particular unequal to 1, as a result of which the rotational speed of the number of turbine blades and the rotational speed of the anode can differ, but at least correlate. The rotational speed of the number of turbine blades and the rotational speed of the anode can in particular correspond. In particular, if the anode and the number of turbine blades are mounted on the rotating shaft, in particular without transmission, the rotational speed of the anode can correspond to the rotational speed of the number of turbine blades. This embodiment is in particular advantageous because a motor of the x-ray tube can be used to rotate the number of turbine blades and the anode. The number of turbine blades and the anode are in particular driven at the same time by the motor of the x-ray tube. The number of turbine blades can be arranged in a distributed manner on a number of turbine blade planes. It is in principle conceivable for the compressor to have, in addition to the rotating turbine blades, static turbine blades in order to force the convection and/or to increase the forced convection. This embodiment can be advantageous in particular for an x-ray emitter with a comparatively high output and corresponding thermal development. The convection is in particular actively forced via the number of turbine blades. A thermal transition coefficient of this embodiment is in particular greater than 300 W/(K*m^2), preferably greater than 1500 W/(K*m^2).

In a preferred embodiment the turbine-shaped compressor and the number of turbine blades of the two previously described embodiments are contained in the x-ray emitter, which can be advantageous in particular for particularly efficient x-ray emitters with a corresponding thermal development. This preferred example embodiment therefore contains an active compressor. In this example embodiment the x-ray emitter is embodied so that the x-ray emitter housing and the x-ray tube housing are embodied as turbine-shaped compressors for forcing the convection and that the anode rotates with the shaft which rotates relative to the x-ray emitter housing, wherein the compressor has the number of turbine blades for forcing the convection and wherein the number of turbine blades are mounted on the rotating shaft so that the rotational speed of the anode corresponds to the rotational speed of the compressor. A thermal transition coefficient of this embodiment is in particular greater than 300 W/(K*m^2), preferably greater than 1500 W/(K*m^2).

One embodiment provides that the x-ray tube is embodied as a rotary piston x-ray tube, wherein a rotational speed of the x-ray tube housing corresponds to the rotational speed of the anode. Advantageously only one motor for the rotation of the anode and the turbine blades and in particular for the rotation of the x-ray tube housing is present in the rotary piston x-ray tube. This embodiment is particularly advantageous because with the rotary piston x-ray tube the evacuated x-ray tube housing rotates together with the anode relative to the x-ray emitter housing. A variable resistance as a result of the gaseous cooling medium is preferably lower compared with a variable resistance as a result of a conventional liquid cooling medium. The rotary piston x-ray tube can preferably rotate more easily. A motor power of the rotary piston x-ray tube can advantageously therefore be less and/or the associated motor can be more favorable. A further advantage is typically that a peek sleeve of the rotary piston x-ray tube can be omitted. The peek sleeve usually has polyetheretherketone, which is in particular a thermoplastic plastic resistant to high temperatures and/or is usually mounted rotatably in a conventional x-ray emitter as an additional sleeve of the x-ray tube housing in order to reduce a drive power of the conventional x-ray tube.

An alternative embodiment for embodiment as a rotary piston x-ray tube provides that the x-ray tube is embodied as a rotary anode x-ray tube, wherein the x-ray tube housing is stationary relative to the x-ray emitter housing. In this case the evacuated x-ray tube housing does not rotate relative to the x-ray emitter housing. Advantageously only one motor for the rotation of the anode and the turbine blades is present in the rotary piston x-ray tube.

One embodiment provides that the x-ray tube housing has an x-ray exit window, wherein the x-ray emitter, in addition to the compressor, has a cooling plate with a number of holes for impingement cooling and wherein the cooling plate with the number of holes is aligned relative to the x-ray exit window so that a gaseous flow directed through the cooling plate as a function of the forced convection strikes the x-ray exit window for impingement cooling purposes. The x-ray exit window is typically illuminated by the x-rays in order to leave the x-ray tube housing, wherein the x-ray exit window is typically heated. This embodiment preferably enables adequate cooling of the x-ray exit window with the gaseous cooling medium, in particular for consecutive imaging examinations with x-ray radiation. A thermal transition coefficient of this embodiment is in particular greater than 300 W/(K*m^2), preferably greater than 1500 W/(K*m^2).

One embodiment provides that in addition to the compressor the x-ray emitter has a cooling plate with a number of needles for a pin-fin cooling and that the number of needles of the cooling plate are fastened to the x-ray tube housing so that a gaseous flow directed between the needles as a function of the forced convection strikes the x-ray tube housing for cooling purposes. The cooling plate can be arranged in particular on the exterior of the x-ray tube housing at a height between the anode and the cathode. A thermal transition coefficient of this embodiment is in particular greater than 300 W/(K*m^2), preferably greater than 1500 W/(K*m^2).

The inventive computed tomography device has a stationary carrier ring and a rotating carrier ring, wherein the rotating carrier ring has the x-ray emitter and an x-ray detector. Attenuation profiles generated with the x-rays are typically detected on the x-ray detector, wherefrom an x-ray beam-based image can be reconstructed. The x-ray beam-based image can be provided for instance on a display unit and/or stored in a storage unit. Advantageously a motor power of a motor of the computed tomography device can be reduced for providing an intrinsic rotation of the rotating part because the x-ray emitter is cooled with the gaseous cooling medium, instead of with the conventional liquid cooling medium, and is therefore typically lighter. The rotating carrier ring can preferably be smaller and/or lighter and/or less stable if the x-ray emitter is lighter.

One embodiment provides that the computed tomography device is embodied so that the convection of the gaseous cooling medium forced by the compressor of the x-ray emitter is amplified by an intrinsic rotation of the rotating carrier ring. The intrinsic rotation of the rotating carrier ring can preferably provide an air flow on the intake side of the compressor so that the pressure on the pressure side of the compressor is increased and/or the cooling by the compressor is therefore amplified. The intrinsic rotation of the rotating carrier ring describes in particular a rotation of the carrier ring with the x-ray emitter by 360°. A frequency of the intrinsic rotation amounts in particular to more than 0.1 Hz, preferably more than 1 Hz, particularly advantageously more than 5 Hz. The x-ray emitter can be arranged on the rotating carrier ring for instance so that the intake side of the compressor is arranged in the rotation direction of the computed tomography device and the pressure side of the compressor is arranged counter to the rotation direction. Alternatively or in addition, the rotating carrier ring and/or the stationary carrier ring can have a profiling in particular on a radial exterior in order to generate the air flow with the intrinsic rotation. It is conceivable for the rotating carrier ring and/or the stationary carrier ring to have further turbine blades in particular on the radial exterior, in order to generate the air flow with the intrinsic rotation.

FIG. 1 shows an x-ray emitter 10 in a first example embodiment. The x-ray emitter 10 has an x-ray tube 11 and an x-ray emitter housing G10. The x-ray tube 11 has an evacuated x-ray tube housing G11, a cathode K for emitting electrons E and an anode A for generating x-rays as a function of the electrons E. The electrons E are emitted by the cathode K when a heating current IH is applied and are accelerated to the anode A by an acceleration voltage supply (not shown).

The x-ray emitter housing G10 has the x-ray tube 11 and outside of the x-ray tube 11 a gaseous cooling medium L. The gaseous cooling medium L circulates the x-ray tube housing G11 in order to cool the x-ray tube 11. The gaseous cooling medium L is outside of the evacuated x-ray tube housing G11.

The x-ray emitter 10 has a compressor V for a forced convection of the gaseous cooling medium L for cooling the x-ray tube 11. A pressure ratio between the intake side and the pressure side of the compressor V is greater than 1.3, in a further preferred example embodiment greater than 2. In this example embodiment the compressor V is embodied as part of the x-ray emitter housing G10 and forms an air supply opening 12. An air discharge opening 13 is arranged on a side facing the intake side. The pressure side of the compressor V is facing the anode A, while the intake side is facing the supply air opening 12. A pressure within the x-ray emitter housing G10 is higher than a pressure outside of the x-ray emitter housing G10. In this example embodiment the active compressor V can comprise an active compressor, for instance. The arrows shown in FIG. 1 show schematically a flow path of the gaseous cooling medium L. The gaseous cooling medium L circulates the x-ray tube 11 for cooling purposes when the convection is forced.

Figure 2:
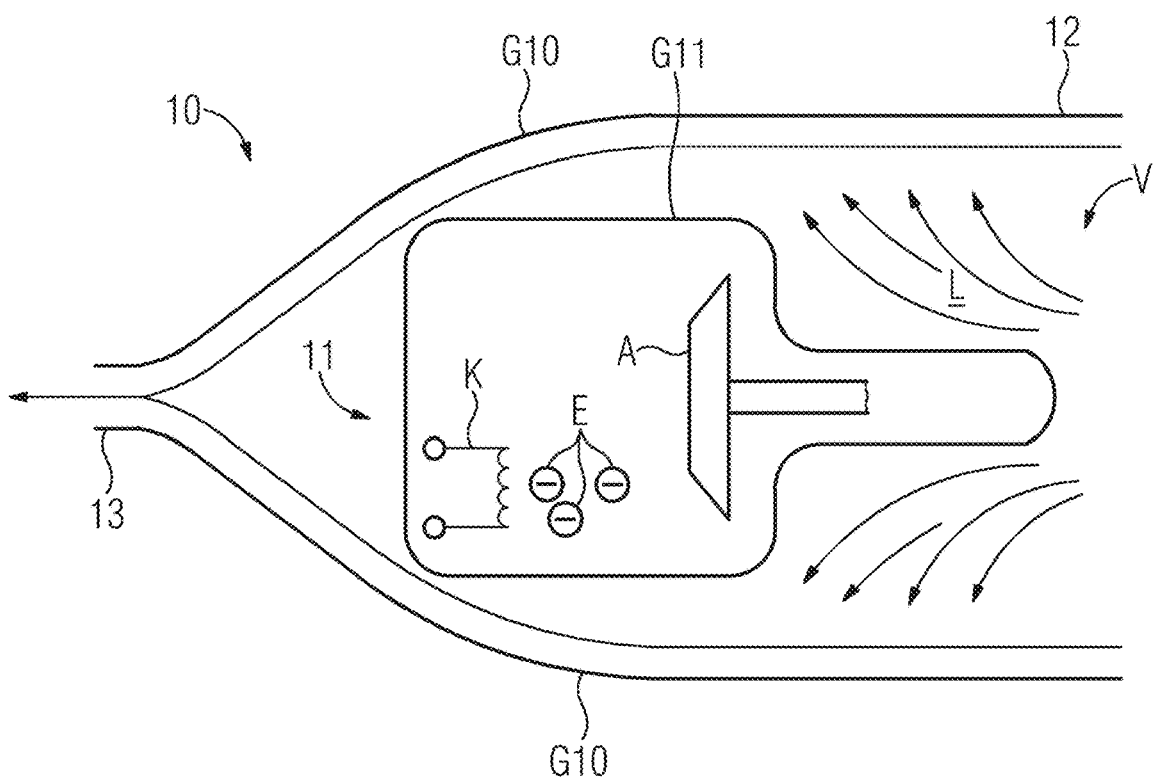
FIG. 2 shows an x-ray emitter 10 in a second example embodiment.

FIG. 2 shows an x-ray emitter 10 in a second example embodiment. The x-ray emitter housing G10 and the x-ray tube housing G11 are embodied as a turbine-shaped compressor V for forcing the convection. The x-ray emitter 10 of the second example embodiment and the x-ray emitter 10 of the first example embodiment differ in particular in that in this example embodiment the convection takes place preferably passively via a turbine-shaped construction of the x-ray emitter housing G10 and the x-ray tube housing G11. The arrows shown in FIG. 2 show schematically a flow profile of the gaseous cooling medium L. In this example embodiment a diameter of the supply air opening 12 is significantly larger than a diameter of the air discharge opening 13. The x-ray emitter housing G10 and the x-ray tube housing G11 together act as a compressor V on account of the turbine-shaped and/or funnel-shaped form. The x-ray emitter housing G10 and the x-ray tube housing G11 each have a tapering cross-section, wherein in this example embodiment an alignment is anti-parallel. It is in principle conceivable for the alignment of the x-ray emitter housing G10 and the x-ray tube housing G11 to be parallel. In this parallel case (not shown), peaks of the x-ray emitter housing G10 and the x-ray tube housing G11 point in the same direction.

Figure 3:
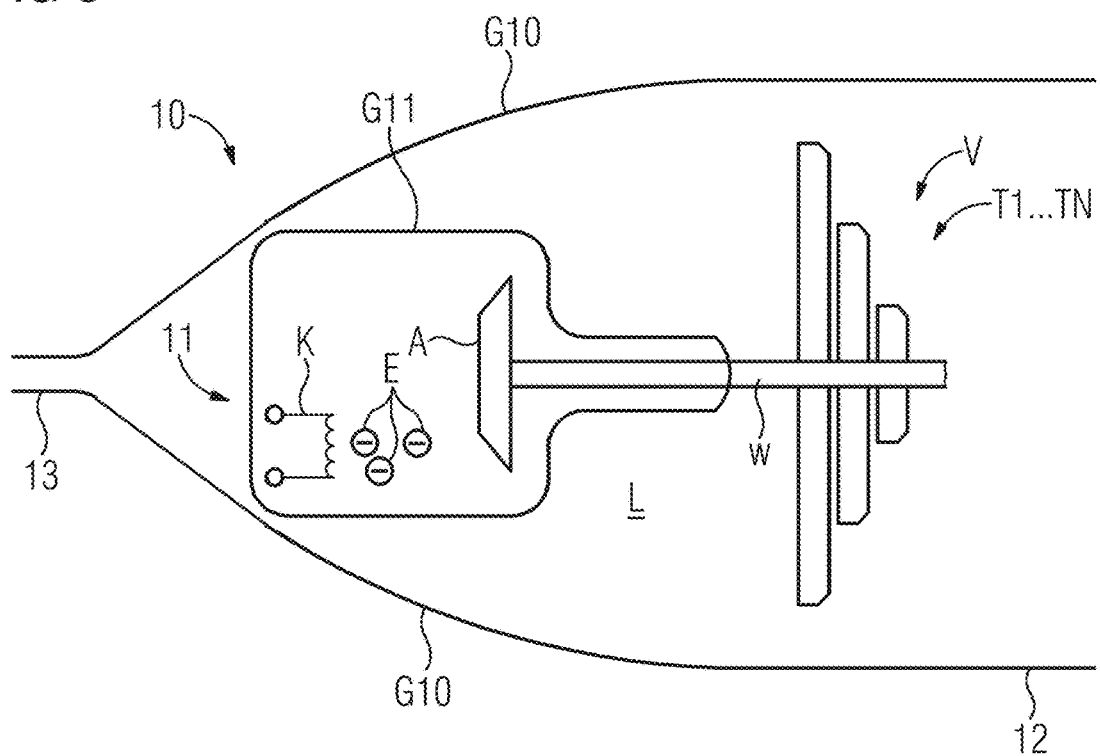
FIG. 3 shows an x-ray emitter 10 in a third example embodiment.

FIG. 3 shows an x-ray emitter 10 in a third example embodiment. This example embodiment is based on the second example embodiment with the turbine-shaped compressor V, wherein in principle another shape of the x-ray emitter housing G10 and/or the x-ray tube housing G11 is conceivable.

The anode A rotates with a shaft W which rotates relative to the x-ray emitter housing G10. The compressor V has a number of turbine blades T1 . . . TN for forcing the convection. The number of turbine blades T1 . . . TN are mounted on the rotating shaft W so that a rotational speed of the anode A and a rotational speed of the compressor V depend on one another. Since the anode A and the number of turbine blades T1 . . . TN are directly connected to the rotating shaft W, in this example embodiment the rotational speed of the anode A corresponds to the rotational speed of the compressor V. An axis of rotation of the anode corresponds to an axis of rotation of the turbine blades T1 . . . TN. The number of, in this example embodiment 6, turbine blades T1 . . . TN are arranged axially offset in FIG. 3 in three turbine blade planes. An angle in an axial cut between the respective turbine blades T1 . . . Tn is typically the same. The turbine blades T1 . . . TN can be arranged at a pitch of less than 90° on the rotating shaft W. The in particular active compressor V has for instance more than 1, preferably 2 to 36, particularly advantageously 20 to 26 turbine blades T1 . . . TN.

This example embodiment can in principle correspond to an embodiment, wherein the x-ray tube 11 is embodied as a rotary anode x-ray tube and wherein the x-ray tube housing G11 is fixed relative to the x-ray emitter housing G12. In this case in particular the anode A and the number of turbine blades T1 . . . TN rotate relative to the x-ray emitter housing G10. The x-ray tube housing G11 and the x-ray emitter housing G11 is stationary so that they cannot be rotated relative to one another.

Figure 4:
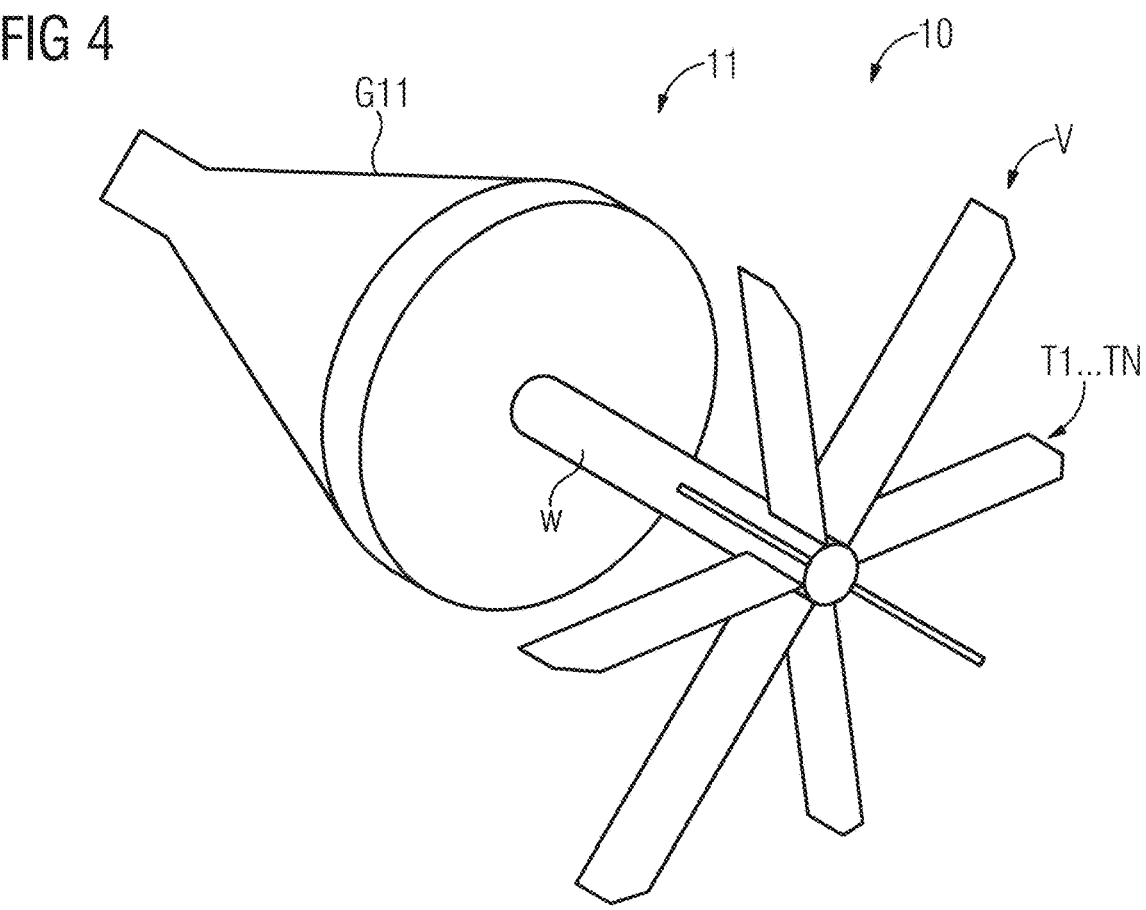
FIG. 4 shows an x-ray emitter 10 in a fourth example embodiment.

FIG. 4 shows a perspective view of an x-ray emitter 10 in a fourth example embodiment. For the sake of clarity FIG. 4 shows a further development of the third example embodiment without the x-ray emitter housing G10. FIG. 4 shows eight turbine blades T1 . . . TN arranged radially about the shaft W in a turbine blade plane.

In this example embodiment, the x-ray tube 11 is embodied as a rotary piston x-ray tube, wherein a rotational speed of the x-ray tube housing G11 corresponds to the rotational speed of the anode A. The anode A rotates mutually with the turbine blade T1 . . . TN and with the x-ray tube housing G11 about a shared axis of rotation, for instance the axis of rotation of the anode A. The cathode K which is not shown in FIG. 4 is typically arranged on the shared axis of rotation and the emitted electrons E are deflected into an edge region of the anode A via an electromagnetic deflection unit. The rotary piston x-ray tube shown in FIG. 4 is essentially cone-shaped. It is in principle possible for a rotary piston x-ray tube to be essentially double cone-shaped.

Figure 5:
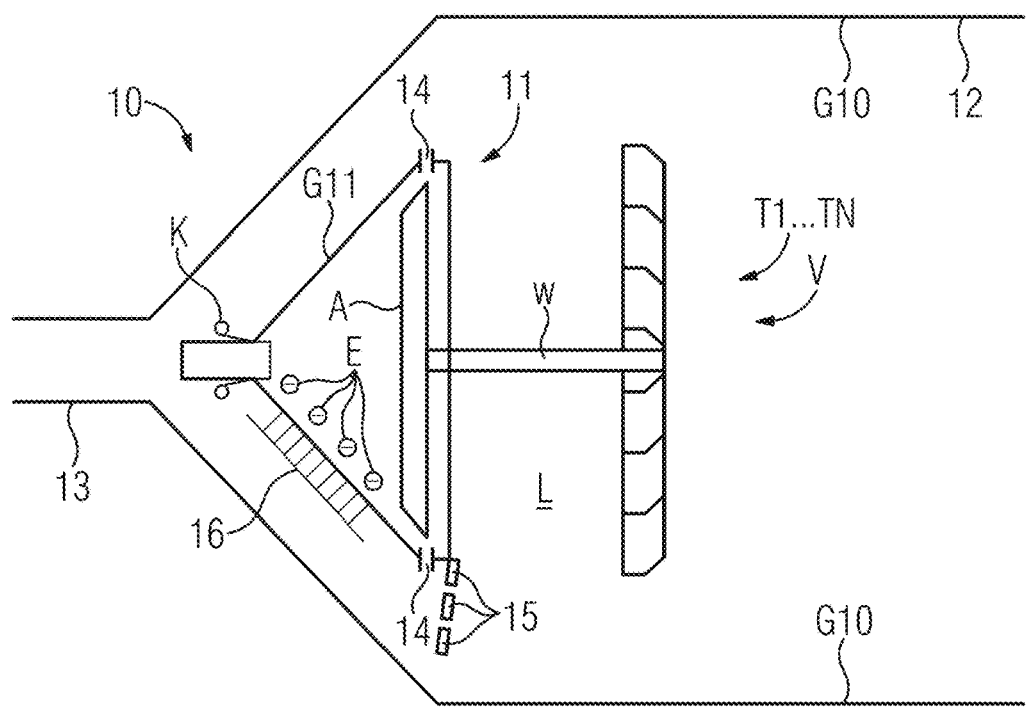
FIG. 5 shows an x-ray emitter 10 in a fifth example embodiment.

FIG. 5 shows an x-ray emitter 10 in a fourth example embodiment. FIG. 5 shows a development of the example embodiment shown in FIG. 4.

The x-ray tube housing G11 has an x-ray beam exit window 14. The x-ray emitter 10 has, in addition to the compressor V, a cooling plate 15 with a number of holes for an impingement cooling. The cooling plate 15 with the number of holes is aligned relative to the x-ray beam exit window 14 so that a gaseous current directed by the cooling plate 15 as a function of the forced convection strikes the x-ray beam exit window 14 for impingement cooling. The x-ray beam exit window 14 typically has glass, titanium, beryllium, aluminum, steel and/or a combination of these elements. The x-ray beam exit window 14 is embodied in a ring-shaped manner. The x-ray tube housing G1 and the x-ray beam exit window 14 are embodied so that the enclosed vacuum is retained. The cooling plate 15 with the number of holes in shown in FIG. 5 in a cross-section and therefore with interruptions in the holes. The cooling plate 15 typically encloses the number of holes. The cooling plate 15 typically has metal, in particular aluminum and/or copper, plastic, polyetheretherketone, carbon-reinforced fibers, a stable material and/or a combination of these materials and/or more than 2 holes. A diameter of at least one hole of the number of holes of the cooling plate 15 lies for instance between 0.1 mm and 40 mm, preferably 1 mm and 4 mm, particularly advantageously between 2 mm and 3 mm. The cooling plate 15 can be rotationally symmetrical. The cooling plate 15 with the number of holes is arranged so that at least the majority of the x-rays miss the cooling plate 15 and in particular do not strike the cooling plate 15. The x-ray emitter 10 is preferably embodied so that the x-ray beams can be detected outside of the x-ray emitter housing G10 and are not completely absorbed within the x-ray emitter housing G10.

In this example embodiment, the x-ray emitter 10, in addition to the compressor V, has a cooling plate 16 with a number of needles for a pin-fin cooling. The number of needles of the cooling plate 16 are fastened with the x-ray tube housing G11 so that a gaseous flow directed between the needles as a function of the forced convection strikes the x-ray tube housing G11 for cooling purposes. The cooling plate 16 is arranged in the region of the tapering x-ray tube housing G11. The cooling plate 16 can be rotationally symmetrical. The cooling plate 16 is aligned with the pressure side of the compressor V so that the gaseous cooling medium with the increased pressure flows through between the cooling plate 16 and the exterior of the x-ray tube housing G11. The cooling plate 16 with the number of needles typically has metal, in particular aluminum and/or copper, plastic, polyetheretherketone, carbon-reinforced fibers, a stable material and/or a combination of these materials and/or more than 1 needle. A diameter of at least one needle of the number of needles of the cooling plate 16 lies for instance between 0.1 mm and 2 mm, preferably between 0.5 mm and 2 mm, particularly advantageously between 1 mm and 1.5 mm. A length of the at least one needle of the number of needles of the cooling plate 16 lies for instance between 0.1 mm and 50 mm, preferably 0.5 mm and 5 mm, particularly advantageously between 2 mm and 4 mm.

It is essentially conceivable for the cooling plate 15 with the number of holes and/or the cooling plate 16 with the number of needles to be arranged on a side of the x-ray tube housing G11 in a vicinity of the anode A.

Figure 6:
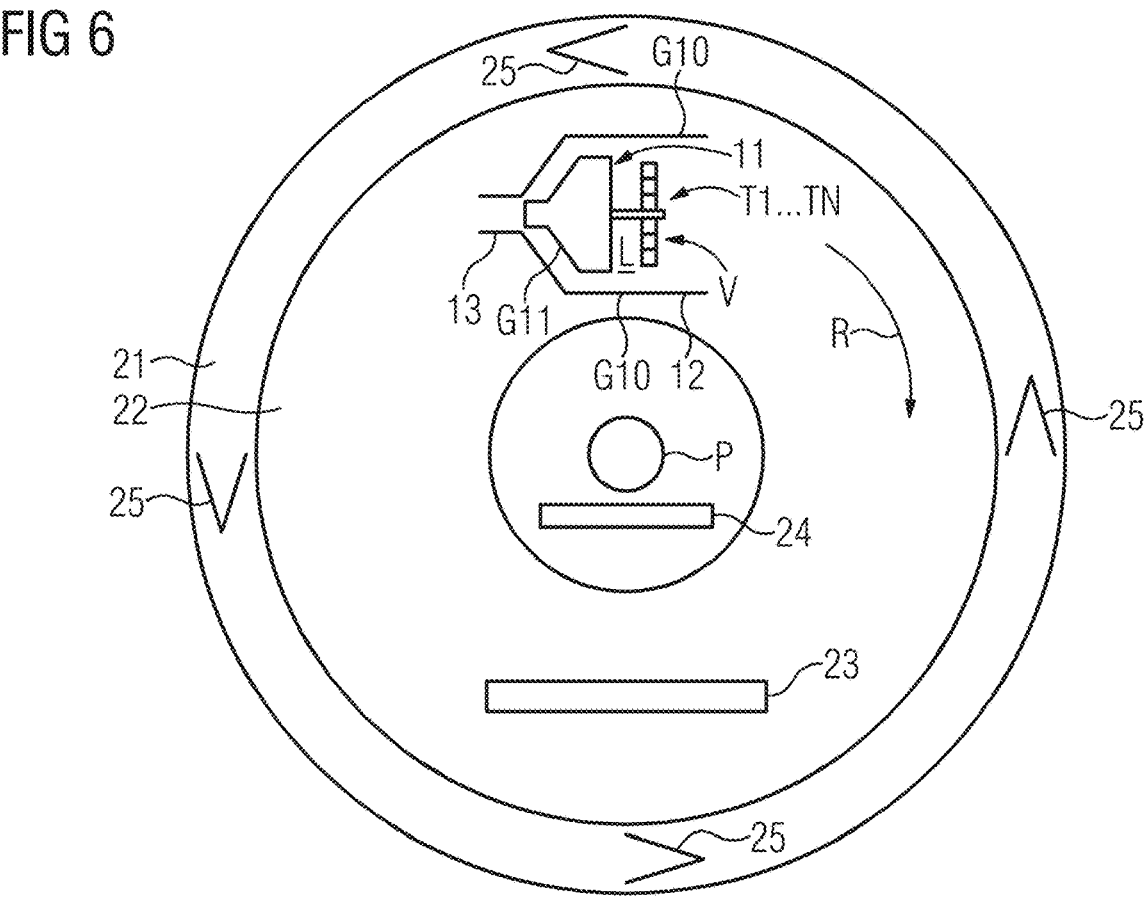
FIG. 6 shows a computed tomography device 20 in a sixth example embodiment.

FIG. 6 shows a computed tomography device 20 in a sixth example embodiment. The computed tomography device 20 has a stationary carrier ring 21 and a rotating carrier ring 22. The stationary carrier ring 21 and the rotating carrier ring 22 have for instance metal and/or plastic and are typically rotationally symmetrical. The computed tomography device shows the rotating carrier ring 22 without a computed tomography device housing.

The rotating support ring 22 has an x-ray emitter 10 and an x-ray detector 23. A patient P is mounted on a patient couch 24 between the x-ray emitter 10 and the x-ray detector 23. Alternatively to the patient P, an object, for instance a suitcase, can be irradiated with the x-ray beams.

In this example embodiment, the computed tomography device 20 is embodied so that the convection of the gaseous cooling medium L which is forced by the compressor V of the x-ray emitter 10 is amplified by an intrinsic rotation of the rotating carrier ring 22. The supply air opening 12 is aligned for this purpose, so that the gaseous cooling medium L is guided and/or pressed into the x-ray emitter housing G10 with the intrinsic rotation of the rotating carrier ring 22. In this example embodiment, the stationary carrier ring 21 has an optional profiling 25, in order additionally to amplify the forced convection. Alternatively or in addition, the rotating carrier ring can have a profiling. The profiling 25 can in particular be embodied so that the gaseous cooling medium L is guided and/or pressed into the x-ray emitter housing G10. The profiling 25 can in particular have further turbine blades and/or be shaped like a shaft and/or worm.

On account of the number of turbine blades T1 ... TN of the compressor V, the compressor is an active compressor. If the number of turbine blades T1 ... TN is replaced by static turbine blades, the passive compressor can be embodied for cooling the x-ray emitter 10, particularly if the convection of the gaseous cooling medium L forced by the compressor V of the x-ray emitter 10 is amplified by the intrinsic rotation of the rotating carrier ring 22.

Although the invention has been illustrated and described in detail using the preferred example embodiments, the invention is not limited by the disclosed examples, and a person skilled in the art can derive other variations therefrom that are still covered by the scope of protection of the invention.

The invention was illustrated and described herein before in detail with reference to example embodiments. It is understood that in particular the description with reference to the figures is for illustrative purposes only and shall not be interpreted in a limiting sense. Variations and combinations may be derived from the information disclosed herein before by the skilled person without departing form the scope or core ideas of present the invention, which are in particular reflected in the appended claims.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray emitter, comprising:
an x-ray tube, the x-ray tube including a cathode for emitting electrons, an anode for generating x-rays as a function of the electrons, and an evacuated x-ray tube housing including an x-ray beam exit window;
an x-ray emitter housing, housing the x-ray tube and including a gaseous cooling medium external to the x-ray tube;
a compressor configured to cause a forced convection of the gaseous cooling medium for cooling the x-ray tube, a pressure ratio between an intake side and a pressure side of the compressor being greater than 1.3; and
a cooling plate including a number of holes for impingements cooling,
wherein the gaseous cooling medium is configured to cool the x-ray tube without a liquid cooling medium, and
wherein the cooling plate is aligned relative to the x-ray beam exit window so that a gaseous flow directed through the cooling plate as a function of the forced convection strikes the x-ray beam exit window for the impingement cooling.

2. The x-ray emitter of claim 1, wherein the x-ray emitter housing and the x-ray tube housing are turbine-shaped compressors configured to force the convection.

3. The x-ray emitter of claim 1,
wherein the anode is configured to rotate, with a shaft, relative to the x-ray emitter housing,
wherein the compressor includes a number of turbine blades configured to force the convection, and
wherein the number of turbine blades are mounted on the rotating shaft so that a rotational speed of the anode and a rotational speed of the compressor depend on one another.

4. The x-ray emitter of claim 3,
wherein the x-ray tube is a rotary piston x-ray tube, and
wherein a rotational speed of the x-ray tube housing corresponds to the rotational speed of the anode.

5. The x-ray emitter of claim 3,
wherein the x-ray tube is a rotary anode x-ray tube, and
wherein the x-ray tube housing is stationary relative to the x-ray emitter housing.

6. The x-ray emitter of claim 1, wherein the pressure ratio is greater than 2.

7. The x-ray emitter of claim 1, wherein the cooling plate includes a number of needles for a pin-fin cooling, and
wherein the number of needles are fastened to the x-ray tube housing so that a gaseous current directed between the needles as a function of the forced convection strikes the x-ray tube housing for cooling purposes.

8. A computed tomography device, comprising:
a stationary carrier ring; and
a rotating carrier ring, wherein the rotating carrier ring includes the x-ray emitter of claim 1 and an x-ray detector.

9. The computed tomography device of claim 8, wherein the computed tomography device is configured to amplify the convection of the gaseous cooling medium, forced by the compressor of the x-ray emitter, by an intrinsic rotation of the rotating carrier ring.

10. The x-ray emitter of claim 2,
wherein the anode is configured to rotate, with a shaft, relative to the x-ray emitter housing,
wherein the compressor includes a number of turbine blades configured to force the convection, and
wherein the number of turbine blades are mounted on the rotating shaft so that a rotational speed of the anode and a rotational speed of the compressor depend on one another.

11. The x-ray emitter of claim 10,
wherein the x-ray tube is a rotary piston x-ray tube, and
wherein a rotational speed of the x-ray tube housing corresponds to the rotational speed of the anode.

12. The x-ray emitter of claim 10,
wherein the x-ray tube is a rotary anode x-ray tube, and
wherein the x-ray tube housing is stationary relative to the x-ray emitter housing.

13. The x-ray emitter of claim 2, wherein the pressure ratio is greater than 2.

14. The x-ray emitter of claim 2, wherein the cooling plate includes a number of needles for a pin-fin cooling, and
wherein the number of needles are fastened to the x-ray tube housing so that a gaseous current directed between the needles as a function of the forced convection strikes the x-ray tube housing for cooling purposes.

15. A computed tomography device, comprising:
a stationary carrier ring; and
a rotating carrier ring, wherein the rotating carrier ring includes the x-ray emitter of claim 2 and an x-ray detector.

16. The computed tomography device of claim 15, wherein the computed tomography device is configured to amplify the convection of the gaseous cooling medium, forced by the compressor of the x-ray emitter, by an intrinsic rotation of the rotating carrier ring.

17. A computed tomography device, comprising:
a stationary carrier ring; and
a rotating carrier ring, wherein the rotating carrier ring includes the x-ray emitter of claim 3 and an x-ray detector.

18. The computed tomography device of claim 17, wherein the computed tomography device is configured to amplify the convection of the gaseous cooling medium, forced by the compressor of the x-ray emitter, by an intrinsic rotation of the rotating carrier ring.

* * * * *